US012661263B2

(12) United States Patent
Kooner et al.

(10) Patent No.:  US 12,661,263 B2
(45) Date of Patent:       Jun. 23, 2026

(54) EYE SHUNT SYSTEM AND METHODS

(71) Applicants: The Board of Regents of The University of Texas System, Austin, TX (US); THE UNITED STATES GOVERNMENT AS REPRESENTED BY THE DEPARTMENT OF VETERANS AFFAIRS, Washington, DC (US)

(72) Inventors: Karanjit S. Kooner, Plano, TX (US); Michael A. Mong, Grapevine, TX (US); Ghadeer Al-Humimat, Dallas, TX (US); Jacob A. Awkal, Plano, TX (US); Hebah G. Abdallah, Carrollton, TX (US); Nguyen L. Le, Richardson, TX (US); Jamasp Azarnoosh, Dallas, TX (US); Peter Dirk Jan Reyntjens, Richardson, TX (US); Jeremy L. Warren, El Paso, TX (US)

(73) Assignees: The Board Regents of The University of Texas System, Austin, TX (US); THE UNITED STATES GOVERNMENT AS REPRESENTED BY THE DEPARTMENT OF VETERAN AFFAIRS, Washinton, DC (US)

( * ) Notice: Subject to any disclaimer, the term of this patent is extended or adjusted under 35 U.S.C. 154(b) by 635 days.

(21) Appl. No.: 18/000,671

(22) PCT Filed: Jun. 4, 2021

(86) PCT No.: PCT/US2021/035857
§ 371 (c)(1),
(2) Date: Dec. 2, 2022

(87) PCT Pub. No.: WO2021/247972
PCT Pub. Date: Dec. 9, 2021

(65) Prior Publication Data
US 2023/0255825 A1      Aug. 17, 2023

Related U.S. Application Data
(60) Provisional application No. 63/034,527, filed on Jun. 4, 2020.

(51) Int. Cl.
A61F 9/007          (2006.01)
(52) U.S. Cl.
CPC ............................... A61F 9/00781 (2013.01)
(58) Field of Classification Search
CPC ................................................... A61F 9/00781
See application file for complete search history.

(56) References Cited

U.S. PATENT DOCUMENTS

| 7,641,627 B2 | 1/2010 | Camras et al. |
| 8,915,877 B2 | 12/2014 | Cunningham, Jr. |

(Continued)

FOREIGN PATENT DOCUMENTS

| CN | 201832016 U | * | 5/2011 |
| WO | 93/03778 A1 | | 3/1993 |
| WO | 2021/247972 A1 | | 12/2021 |

OTHER PUBLICATIONS

Extended European Search Report for European Application No. 21817556, mailed Apr. 26, 2024, 11 pages.

(Continued)

*Primary Examiner* — Leslie R Deak
(74) *Attorney, Agent, or Firm* — BALLARD SPAHR LLP

(57)               ABSTRACT
A shunt operable to be implanted on an eye is provided. The shunt includes a vein fluidic channel operable to be in fluid communication with an interior of the eye and operable to receive aqueous fluid from the interior of the eye. A body is fluidly coupled with the vein fluidic channel. A valve is (Continued)

disposed within the body and is operable to regulate intraocular pressure in the eye by opening and closing based on pressure from the aqueous fluid. A plurality of outlets are in fluid communication with the body opposite the vein fluidic channel in relation to the valve. The outlets are operable to release the aqueous fluid to the sclera of the eye.

19 Claims, 11 Drawing Sheets

(56)                References Cited

U.S. PATENT DOCUMENTS

| | | |
|---|---|---|
| 2002/0087111 A1 | 7/2002 | Ethier et al. |
| 2005/0273033 A1* | 12/2005 | Grahn ................. A61M 27/002 |
| | | 604/9 |
| 2012/0245505 A1* | 9/2012 | Robinson ............. A61K 9/0051 |
| | | 604/290 |
| 2015/0112424 A1 | 4/2015 | DeYoung et al. |
| 2016/0101220 A1 | 4/2016 | DeYoung et al. |
| 2018/0271700 A1 | 9/2018 | Alhourani |

OTHER PUBLICATIONS

International Patent Application No. PCT/US2021/035857 "International Search Report and Written Opinion" mailed Sep. 24, 2021, 8 pages.

* cited by examiner

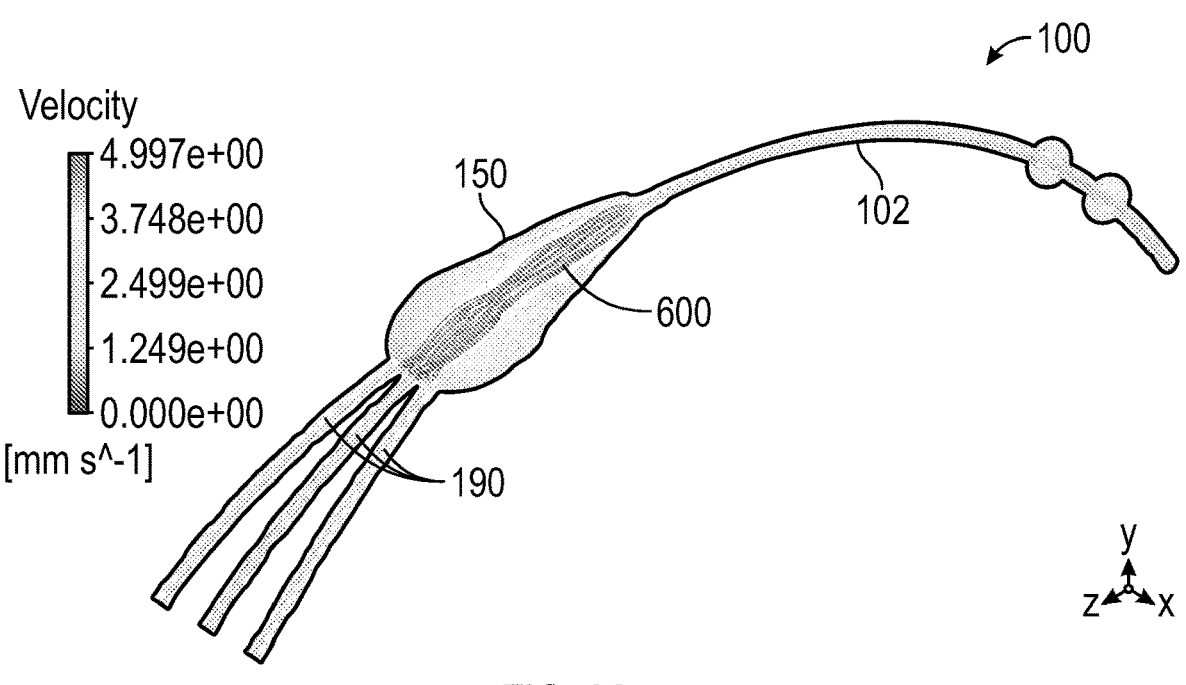
FIG. 6A
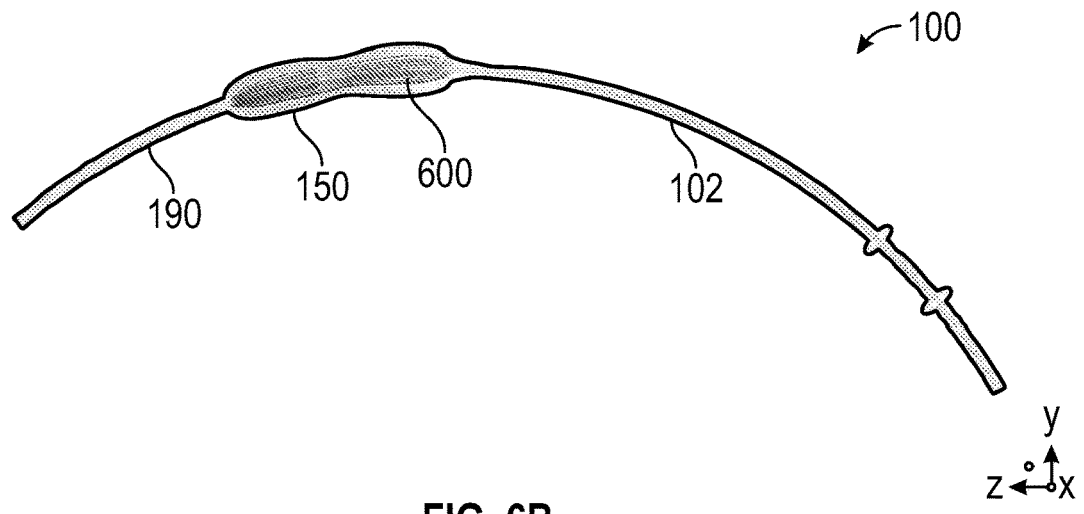
FIG. 6B
FIG. 6C

Von Mises
Stress 5.389e+03

4.041e+03

2.694e+03

1.347e+03

2.501e-06

[Pa]

EYE SHUNT SYSTEM AND METHODS

CROSS REFERENCE TO RELATED APPLICATIONS

The present application is a national stage application filed under 35 U.S.C. § 371 of International Patent Application No. PCT/US2021/035857 entitled "EYE SHUNT SYSTEM AND METHODS" filed Jun. 4, 2021, which claims the benefit of U.S. Provisional Patent Application No. 63/034,527 entitled "EYE SHUNT SYSTEM AND METHODS" filed on Jun. 4, 2020, the contents of which are incorporated by reference in their entireties.

BACKGROUND

1. Field

The present disclosure relates generally to systems and methods related to an eye shunt. In at least one example, the present disclosure relates to a shunt operable to be implanted on an eye with a valve to regulate intraocular pressure in the eye and a plurality of outlets to release aqueous fluid to the sclera of the eye.

2. Discussion of Related Art

Glaucoma is the second most common cause of irreversible blindness, affecting more than 79 million people worldwide including over three million Americans. There are several risk factors associated with glaucoma, e.g., elevated intraocular pressure (IOP), older age, family history, thin central corneal thickness (CCT), myopia, race, hypertension, and diabetes. IOP is, to date, the primary modifiable risk factor and typically is initially treated with topical medications, followed by laser therapy and finally, with surgical interventions. The conventional surgical options can include trabeculectomy and glaucoma drainage devices.

Trabeculectomy can be invasive and involves creating an opening into the anterior chamber (AC) of the eye from underneath a partial thickness scleral flap, to allow aqueous fluid to flow into the subconjunctival space. The aqueous fluid is highly inflammatory and together with extensive tissue manipulation, the eye can respond with exuberant and uncontrolled fibrosis. As a result, a considerable amount of attention has been given to the pharmacologic modulation of wound healing to minimize surgical failure. However, these measures can be associated with short and long term complications, e.g., bleb failure, wound leaks, and endophthalmitis.

Glaucoma drainage devices, such as shunt implants, can be less invasive than trabeculectomy procedures, but can be bulky, requiring considerable surgical dissection.

BRIEF SUMMARY

The present inventive concept provides a shunt operable to be implanted on an eye. A vein fluidic channel receives aqueous fluid from the eye which is passed to a body of the shunt. A plurality of retainers extend from the vein fluidic channel and are positioned to maintain the position of the vein fluidic channel and the shunt. A valve disposed in the body regulates intraocular pressure in the eye by opening and closing based on pressure from the aqueous fluid. The aqueous fluid, after passing through the valve in the body, exits the shunt through a plurality of outlets. The plurality of outlets sprinkle the aqueous fluid on the sclera at a predetermined distance of at least 10 millimeters from the cornea such that the aqueous fluid is absorbed by fat and taken back by the venous system.

The aforementioned may be achieved in an aspect of the present inventive concept by providing a shunt operable to be implanted on an eye. The shunt may include a vein fluidic channel operable to be in fluid communication with an interior of the eye and may be operable to receive aqueous fluid from the interior of the eye. A body may be fluidly coupled with the vein fluidic channel, and a valve may be disposed within the body. The valve may be operable to regulate intraocular pressure (IOP) in the eye by opening and closing based on pressure from the aqueous fluid. A plurality of outlets may be in fluid communication with the body opposite the vein fluidic channel in relation to the valve. The plurality of outlets may be operable to release the aqueous fluid to the sclera of the eye. The plurality of outlets may release the aqueous fluid at least 10 millimeters from the cornea of the eye.

The valve may include two leaflets, where at least a portion of the two leaflets may abut one another when the valve is closed. Each of the two leaflets may have a length that is two times the width of an inner lumen of the body. A base of each of the leaflets may have a base thickness, where the thickness of the leaflets may taper towards an end opposite the base. The end opposite the base of each of the leaflets may have an end thickness that is ⅓ the base thickness. The two leaflets may be operable to deform and separate from one another upon exposure to a predetermined amount of pressure from the aqueous fluid.

At least one of the vein fluidic channel, the body, the valve, and/or the plurality of outlets can be at least partially coated with at least one drug to be released into the aqueous fluid. The drug may include mitomycin-C. The drug may be configured to be released over a predetermined period of time. The predetermined period of time may be up to four weeks.

At least two retainers may extend from the vein fluidic channel. The at least two retainers may be operable to maintain positioning of the vein fluidic channel. The at least two retainers may be substantially circular and extend radially from the vein fluidic channel. The at least two retainers may be positioned such that, when implanted, one of the at least two retainers may be operable to be positioned on the trabecular meshwork surface of the eye and the other of the at least two retainers may be operable to be positioned on the scleral surface of the eye.

A surface of at least one of the vein fluidic channel, the body, and/or the plurality of outlets operable to be placed, when implanted, on the eye may be flat. At least one of the vein fluidic channel, the body, the valve, and/or the plurality of outlets may be made of a bio-compatible material. The material may include a hydrogel. The material may include an acrylic hydrogel or a silicone hydrogel.

The aforementioned may also be achieved in an aspect of the present inventive concept by providing a system including a shunt as disclosed herein, and a forceps operable to implant the shunt in the eye. The forceps may include tips configured to collectively form a hollow body operable to receive, when the tips are in a closed configuration, the vein fluidic channel.

The foregoing is intended to be illustrative and is not meant in a limiting sense. Many features of the embodiments may be employed with or without reference to other features of any of the embodiments. Additional aspects, advantages, and/or utilities of the present inventive concept will be set forth in part in the description that follows and, in part, will be apparent from the description, or may be learned by practice of the present inventive concept.

BRIEF DESCRIPTION OF THE DRAWINGS

The description will be more fully understood with reference to the following figures and data graphs, which are presented as various embodiments of the present inventive concept and should not be construed as a complete recitation of the scope of the present inventive concept, wherein:

FIG. 6A illustrates a perspective view of velocity of fluid flowing through the shunt;

FIG. 6B illustrates a side view of velocity of fluid flowing through the shunt;

FIG. 6C illustrates a top view of velocity of fluid flowing through the shunt;

DETAILED DESCRIPTION

Figure 1A:
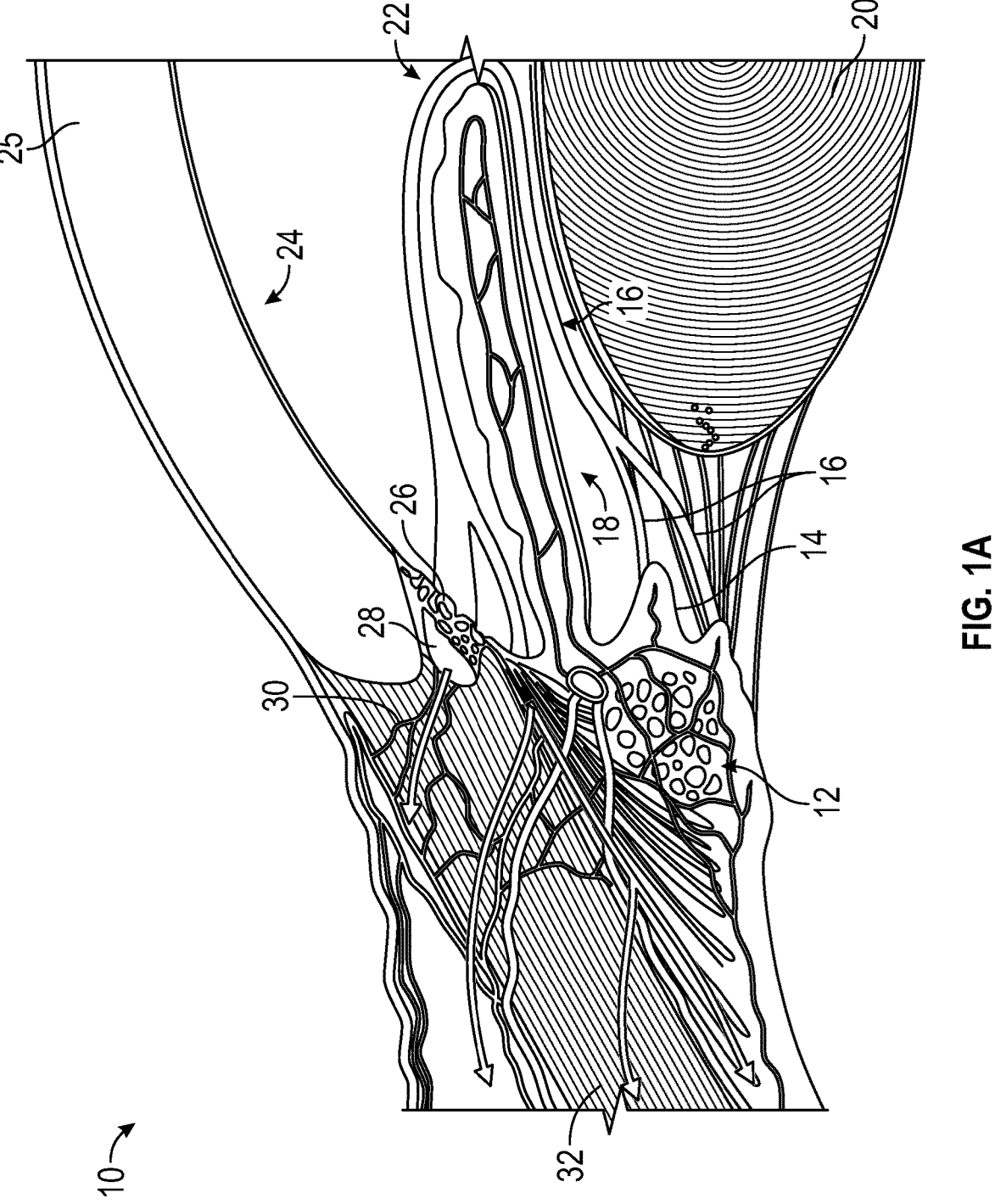
FIG. 1A illustrates an example of a portion of an eye environment in which a shunt may be used in accordance with the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims. Further, it should be understood that any one of the features of the present inventive concept may be used separately or in combination with other features. Other systems, methods, features, and advantages of the present inventive concept will be, or become, apparent to one with skill in the art upon examination of the figures and the detailed description. It is intended that all such additional systems, methods, features, and advantages be included within this description, be within the scope of the present inventive concept, and be protected by the accompanying claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

Any term of degree such as, but not limited to, "substantially," as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees.

The term "coupled" is defined as connected, whether directly or indirectly through intervening components, and is not necessarily limited to physical connections. The connection can be such that the objects are permanently connected or releasably connected. The terms "comprising," "including" and "having" are used interchangeably in this disclosure. The terms "comprising," "including" and "having" mean to include, but not necessarily be limited to the things so described. The term "real-time" or "real time" means substantially instantaneously.

Lastly, the terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps or acts are in some way inherently mutually exclusive.

II. General Architecture

Figure 1B:
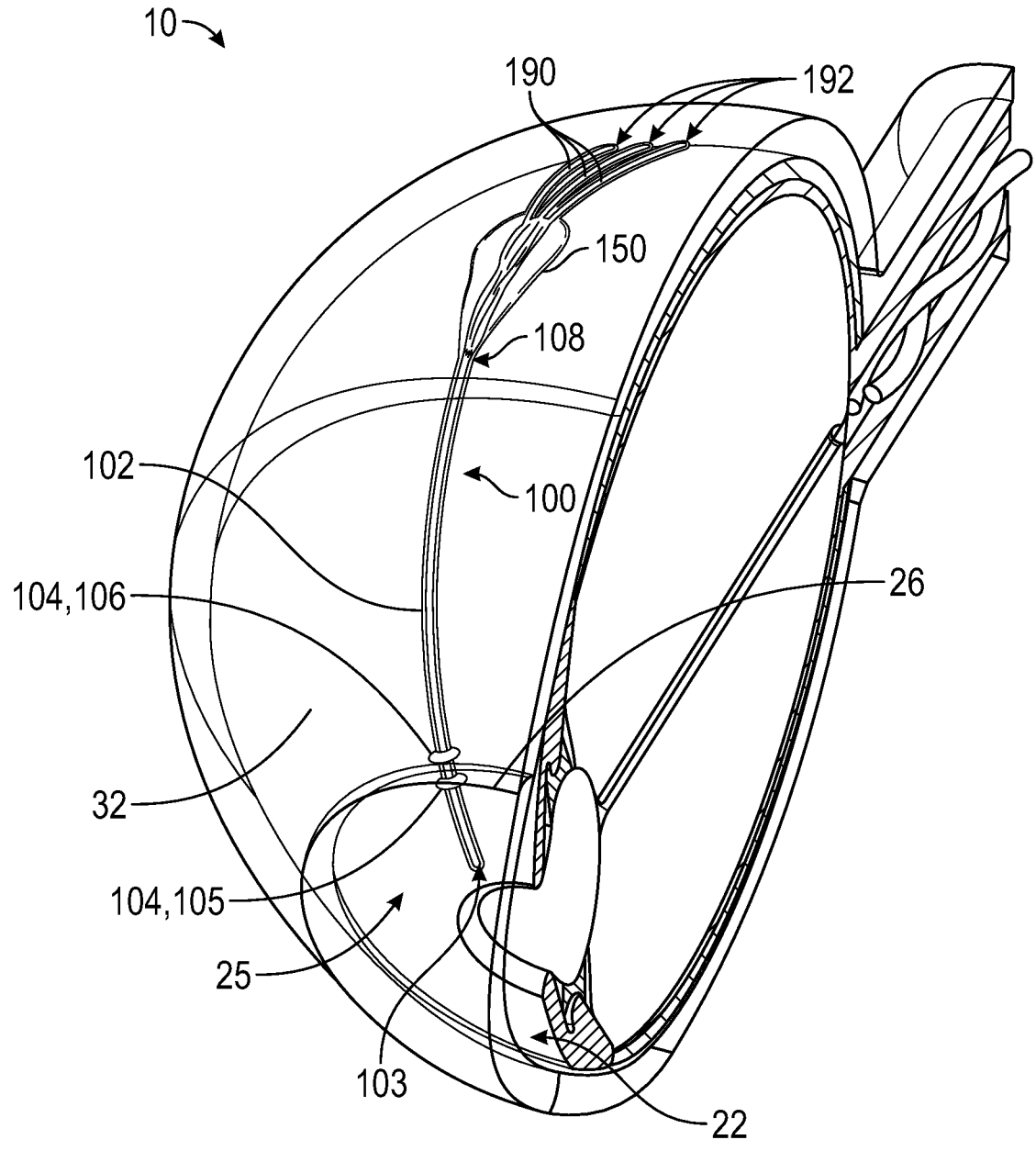
FIG. 1B illustrates an example of a shunt implanted on the eye.

The disclosure now turns to FIGS. 1A and 1B, which illustrate an exemplary eye environment 10 for a shunt 100, in which the present disclosure may be implemented. The eye 10 produces and releases aqueous fluid 16, for example aqueous humor, which provides a transparent and colorless medium between the cornea and the lens. The rate of formation can be about 2 µl/min to about 2.5 µl/min, and a rate of turnover of the aqueous fluid 16 in the eye can be about 1% to about 1.5% of the anterior chamber volume (250 µl) per minute. A flow of the aqueous fluid 16 in humans can follow a circadian rhythm, with rates during sleep being approximately one half of those in the morning. The rate of flow can be as follows: 8 AM to noon=3.0±0.8 µl/min, afternoon=2.7±0.6 µl/min, and midnight to 6 AM=1.3±0.4 µl/min.

The aqueous fluid 16 can be slightly hypertonic compared to plasma. The aqueous fluid 16 can be acidic with a PH of about 7.2. The aqueous fluid 16 can include an excess of ascorbate (Vitamin C) (15 times greater than arterial plasma) and a marked deficit of protein (0.02% compared with 7% in plasma). The aqueous fluid 16 also can have a slight excess of chloride and/or lactic acid, and a slight deficit of sodium, bicarbonate, carbon dioxide, and/or glucose in comparison to plasma. Other reported constituents in the aqueous fluid 16 can be amino acids, sodium hyaluronate, norepinephrine, coagulation properties, and/or tissue plasminogen activator.

The portions of the eye 10 which are related to the aqueous fluid 16 can include a ciliary body 12 and a trabecular meshwork (TM) 26. The ciliary body 12 produces the aqueous fluid 16, and ciliary processes 14 of the ciliary body 12 can secrete the aqueous fluid 16. For example, the aqueous fluid 16 can be derived from plasma within capillary networks of the ciliary processes 14. The aqueous fluid 16 can be secreted from the ciliary processes 14 through diffusion, ultrafiltration, and/or active secretion. Active secretion can contribute, for example, 90% of production and secretion of the aqueous fluid 16.

The aqueous fluid 16 is secreted by the ciliary processes 14 to the posterior chamber 18. The aqueous fluid 16 can pass across the lens 20 through the pupil 22 to the anterior chamber 24. At least a portion of the aqueous fluid 16 leaves the eye 10 at the anterior chamber 24 through the TM 26. The TM 26 can, for example, be responsible for 70%-90% of the outflow of the aqueous fluid 16, depending on the age and/or the health of the eye 10. The aqueous fluid 16 exiting the eye 10 through the TM 26 is dependent on pressure, so the TM 26 is critical for regulation of intraocular pressure (IOP) in the eye 10. Equilibrium of IOP in the eye 10 is achieved between the production and drainage of the aqueous fluid 16. For example, with glaucoma, loss of TM cells can result in fusion and/or thickening of trabecular lamellae which can affect the drainage of the aqueous fluid 16. In turn, the IOP in the eye 10 increases. The shunt 100 can be implanted on the eye 10, for example as illustrated in FIG. 1B, to reduce and/or regulate IOP by releasing the aqueous fluid 16 in a controlled manner from the interior of the eye 10 to a surface of a sclera 32.

Figures 2A, 2B:
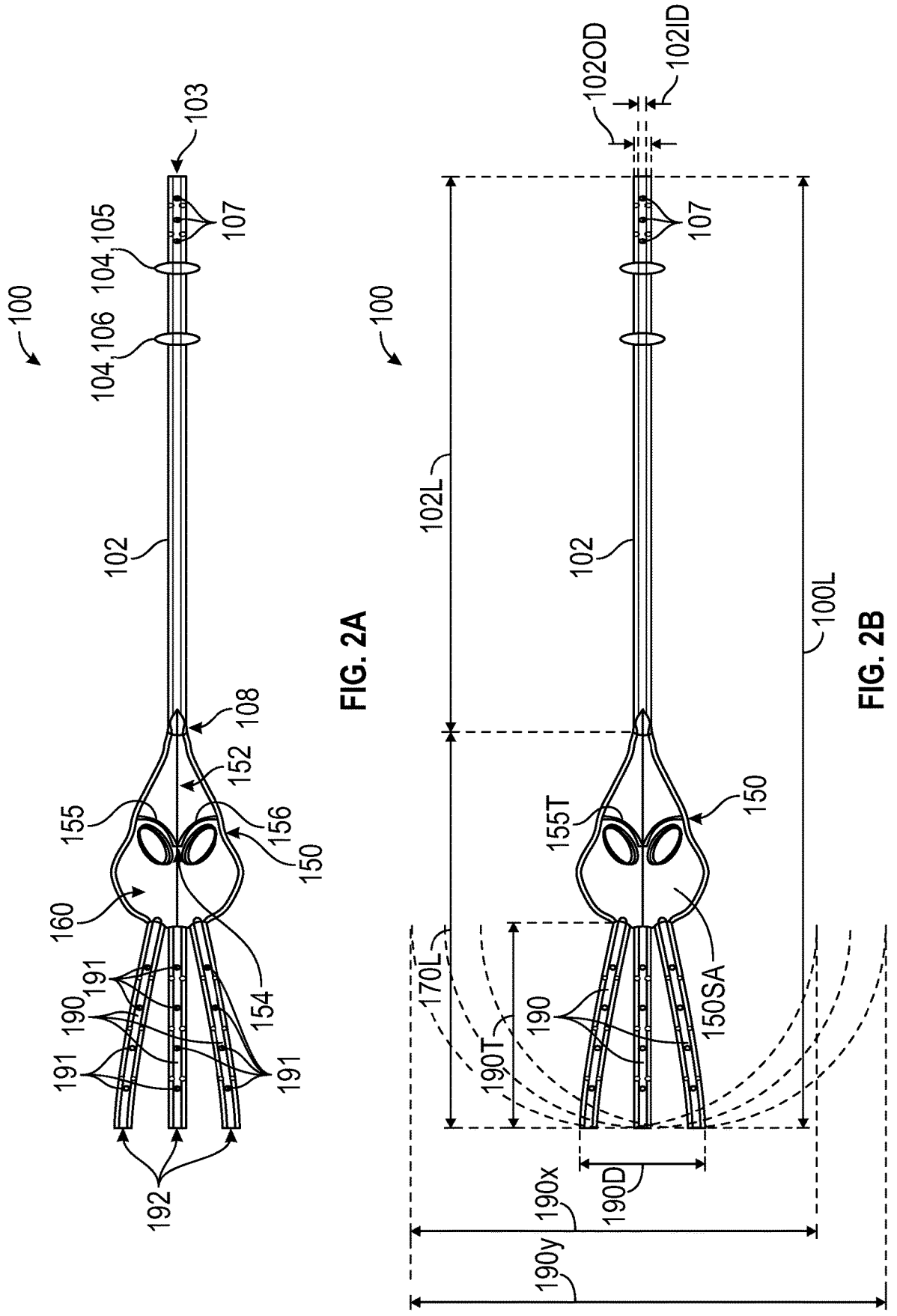
FIGS. 2A and 2B illustrate an example of a shunt.

Referring to FIGS. 1B, 2A, and 2B, the shunt 100 includes a vein fluidic channel 102 operable to be in fluidic communication with the interior of the eye 10, for example the anterior chamber 24, the pupil 22, and/or the TM 26. The vein fluidic channel 102 can receive the aqueous fluid 16 from the interior of the eye 10 to assist in draining the aqueous fluid 16. In at least one example, the vein fluidic channel 102 is biocompatible to prevent the body from rejecting the vein fluidic channel 102. In some examples, the vein fluidic channel 102 can include a medical grade silicone tube. In some examples, the vein fluidic channel 102 can include a portion of a vein taken from the patient.

The vein fluidic channel 102 can have an inner diameter 102ID of about 50 µm to about 300 µm. In some examples, the vein fluidic channel 102 can have an inner diameter 102ID of about 100 µm to about 200 µm. In some examples, the vein fluidic channel 102 can have an inner diameter 102ID of about 125 µm to about 175 µm. In some examples, the vein fluidic channel 102 can have an inner diameter 102ID of about 150 µm.

The vein fluidic channel 102 can have an outer diameter 102OD of about 100 µm to about 500 µm. In some examples, the vein fluidic channel 102 can have an outer diameter 102OD of about 150 µm to about 450 µm. In some examples, the vein fluidic channel 102 can have an outer diameter 102OD of about 220 µm to about 380 µm. In some examples, the vein fluidic channel 102 can have an outer diameter 102OD of about 310 µm.

The vein fluidic channel 102 can have a length 102L of about 3 millimeters (mm) to about 10 mm. In some examples, the vein fluidic channel 102 can have a length 102L of about 4 mm to about 7 mm. In some examples, the vein fluidic channel 102 can have a length 102L of about 5 mm.

The inner diameter 102ID, the outer diameter 102OD, and/or the length 102L of the vein fluidic channel 102 can be provided to mimic the aqueous veins and/or rate of drainage of the aqueous fluid 16 in the human body.

In at least one example, at least two retainers 104 are provided to maintain the positioning of the vein fluidic channel 102 when implanted in the eye 10. The retainers 104 can prevent intrusion or extrusion of the shunt 100 after being implanted in the eye 10. In at least one example, the two retainers 104 can extend from the vein fluidic channel 102. In some examples, the two retainers 104 can be coupled with the vein fluidic channel 102. In at least one example, the retainers 104 can be substantially circular and extend radially from the vein fluidic channel 102. For example, the retainers 104 can be collar-shaped and formed around the vein fluidic channel 102. In other examples, the retainers 104 can have different shapes such as rectangular, oval, triangular, or any other suitable shapes to maintain the positioning of the vein fluidic channel 102. In some examples, the retainers 104 can each have different shapes depending on a surface the retainers 104 are placed on when implanted.

A proximal retainer 105 of the retainers 104 can be disposed towards the inlet 103 of the vein fluidic channel 102, and a distal retainer 106 of the retainers 104 can be disposed distal from the inlet 103 in relation to the proximal retainer 105. For example, the proximal retainer 105 is operable to be positioned on the surface of the TM 26, and the distal retainer 106 is operable to be positioned on the scleral 32. Accordingly, the retainers 104 are held in place by the sclera 32.

In at least one example, the retainers 105, 106 can be provided about 0.7 mm to about 2.5 mm apart from one another. In some examples, the retainers 105, 106 can be provided about 1.1 mm to about 2.1 mm apart from one another. In some examples, the retainers 105, 106 can be provided about 1.5 mm to about 1.65 mm apart from one another.

In at least one example, the proximal retainer 105 can be disposed about 1 mm to about 8 mm from the inlet 103. In some examples, the proximal retainer 105 can be disposed about 3 mm to about 6 mm from the inlet 103. In some examples, the proximal retainer 105 can be disposed about 5 mm from the inlet 103. The portion of the vein fluidic channel 102 between the inlet 103 and the proximal retainer 105 can be disposed interior of the eye 10 when implanted. In at least one example, the portion of the vein fluidic channel 102 can be adjustable in length as desired by the surgeon. In some examples, the vein fluidic channel 102 between the inlet 103 and the proximal retainer 105 can include one or more pores 107 that can provide an alternative conduit for the aqueous fluid 16 to flow into the vein fluidic channel 102 in case the inlet 103 has been blocked.

By utilizing the retainers 104 to maintain position of the vein fluidic channel 102 when implanted, less stitching is required. Accordingly, the procedure to implant the shunt 100 can be performed quicker and with fewer complications.

Figure 2C:
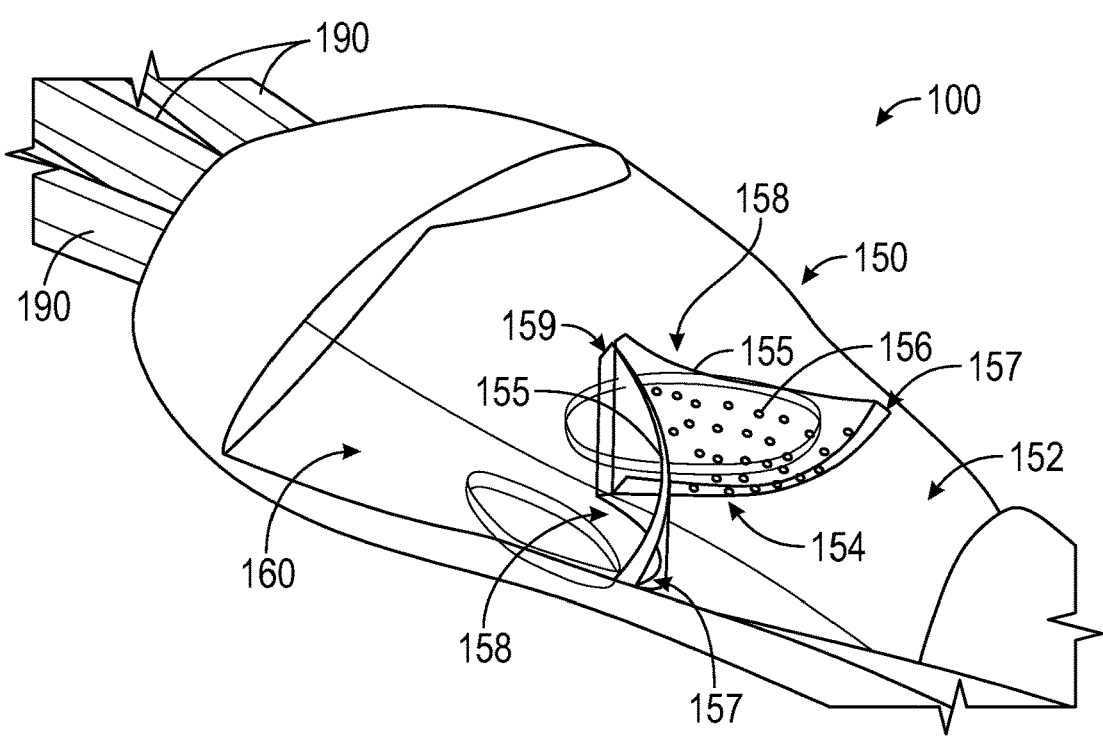
FIG. 2C illustrates an example of a body with a valve of a shunt.

In use, the vein fluidic channel 102 receives the aqueous fluid 16 from the interior of the eye 10 through the inlet 103 and along the length 102L of the vein fluidic channel 102 to a body 150 fluidly coupled with the vein fluidic channel 102, also shown in FIG. 2C. The body 150 receives the aqueous fluid 16 from the vein fluidic channel 102 and controls the flow of the aqueous fluid 16 across the body 150 to assist in regulating IOP in the eye 10.

In at least one example, the body 150 can have a surface area 150SA of about 7 mm² to about 14 mm². In some examples, the body 150 can have a surface area 150SA of about 8.5 mm² to about 11 mm². In some examples, the body 150 can have a surface area 150SA of about 9.81 mm². Accordingly, the body 150 has a small surface area to limit the irritation and entry hole needed during implantation of the shunt 100 on the eye 10.

A valve 154 is disposed in the body 150. The valve 154 is operable to regulate IOP in the eye 10 by opening and closing based on pressure from the aqueous fluid 16. In at least one example, the valve 154 can be configured to be biomimetic to the human venous valve which is bicuspid in shape and crescent shaped with edges that meet at a commissure. The valve 154 separates an entry chamber 152 and an exit chamber 160 in the body 150. The entry chamber 152 is operable to receive the aqueous fluid 16 from the entry 108 of the body 150 fluidly coupled with the vein fluidic channel 102. In at least one example, as illustrated in FIGS. 1B-2C, the entry chamber 152 can have a smaller volume than the exit chamber 160. Accordingly, in some examples, the shape of the body 150 can be substantially triangular such that the body 150 tapers from the exit chamber 160 towards the entry chamber 152. Other shapes of the body 150 can be contemplated without deviating from the scope of the inventive concept.

The valve 154 includes two leaflets 155. At least a portion of each of the two leaflets 155 abut one another when the valve 154 is closed, preventing the aqueous fluid 16 from flowing across the valve 154. The two leaflets 155 are operable to deform and separate from one another upon exposure to a predetermined amount of pressure from the aqueous fluid 16. The leaflets 155 are configured to be pressure-based such that the leaflets 155 remain closed unless the pressure from the aqueous fluid 16 in the entry chamber 152 exceeds a predetermined threshold. The predetermined threshold is such that the leaflets 155 separate to release the aqueous fluid 16 slowly, maintaining the desired IOP in the eye 10. The precise configuration of the valve 154 and the body 150 provide a high functionality of the valve 154 that regulates IOP in a slow unidirectional fashion.

A base 157 of the leaflets 155 can have a base thickness. In at least one example, the thickness 154T of each of the leaflets 155 can taper towards an end opposite the base 157, where the ends opposite the base 157 meet at the commissure 159 to close the valve 154. In at least one example, the end opposite the base 157 of each of the leaflets 155 has an end thickness that is ⅓ the base thickness. In at least one example, each of the two leaflets 155 can have a length that is about two times the width of an inner lumen of the body 150. In some examples, the valvular sinus 158 which is the space between the leaflets 155 and the body 150 can be thin.

The aqueous fluid 16 flows, when the valve 154 opens, from the entry chamber 152 to the exit chamber 160 in the body 150. A plurality of outlets 190 are provided in fluid communication with the body 150 opposite the vein fluidic channel 102 in relation to the valve 154. For example, the plurality of outlets 190 can be in fluid communication with the exit chamber 160, separated from the entry chamber 152 and the vein fluidic channel 102 by the valve 154. The outlets 190 can be operable to release the aqueous fluid 16 to the sclera of the eye 10.

The plurality of outlets 190 can include, for example, fluidic channels such as tubes to direct and distribute the aqueous fluid 16 throughout the sclera of the eye 10 to assist in absorption of the aqueous fluid 16. In at least one example, the outlets 190 can each be provided in close proximity to one another at the attachment to the body 150 to provide substantially equal distribution of the aqueous fluid 16 flow through each of the outlets 190. The outlets 190 can be configured such that the outlets 190 can distribute the aqueous fluid 16 across a wide surface area of the eye 10. For example, the outlets 190 can distribute the aqueous fluid 16 across a distribution range 190D of about 4 mm to about 10 mm. In some examples, the distribution range 190D can be about 6 mm to about 8 mm. In some examples, the distribution range 190D can be about 7.28 mm. By distributing or sprinkling the aqueous fluid 16 across a wide distribution range of area of the eye 10, the shunt 100 prevents inflammation.

In at least one example, as illustrated in FIG. 2B, the outlets 190 may be rigid and inflexible such that each of the outlets 190 may not be movable relative to each other. In at least one example, as illustrated in FIG. 2B, the outlets 190 may each be flexible such that each of the outlets 190 may be independently movable relative to each other to direct the aqueous fluid 16 to a desired portion of the eye 10. For example, the broken lines in FIG. 2B illustrate exemplary ranges of motion and/or distribution ranges for each of the outlets 190. Distribution range 190x shows the maximum range of motion and/or range of distribution for one of the outlets 190. Range of motion and/or range of distribution 190y shows the maximum range of motion and/or range of distribution for the combination of the plurality of outlets 190. In combination, the range of motion and/or range of distribution 190y achieved by the plurality of outlets 190 permits a greater surface area for distributing the aqueous fluid 16 to different portions of the eye 10. Accordingly, inflammation can be better prevented. In at least one example, a medical professional may adjust any or each of the outlets 190 prior to implantation of the shunt 100 based on previous analysis of the patient's eye 10. In some examples, the medical professional may adjust any or each of the outlets 190 after implantation of the shunt 100 to ensure the correct placement of the outlets 190 to control the release of the aqueous fluid 16.

In at least one example, any of the outlets 190 may be movable or rotatable while releasing the aqueous fluid 16. For example, as the aqueous fluid 16 is being released through the outlets 190, any combination of the outlets 190 may move such that the aqueous fluid 16 being released from each individual outlet 190 is not being continuously deposited in the same spot on the eye 10. The outlets 190 may then release the aqueous fluid 16 across a wide surface area across the eye 10 to prevent inflammation.

FIGS. 1B-2C illustrate the shunt 100 with three outlets 190. In other examples, the shunt 100 can include two outlets 190. In yet other examples, the shunt 100 can include more than three outlets 190, for example up to nine outlets 190.

In some examples, the outlets 190 can be tapered from body 150 towards the tips 192 of the outlets 190 where the aqueous fluid 16 is released. In some examples, the tips 192 of the outlets 190 can be rounded. In some examples, the outlets 190 can include a plurality of pores 191 operable to assist in distributing the aqueous fluid 16.

In at least one example, the outlets 190 can have a length 190T of about 2 mm to about 9 mm. In some examples, the outlets 190 can have a length 190T of about 4 mm to about 6 mm. In some examples, the outlets 190 can have a length 190T of about 5 mm.

The outlets 190 and the body 150 can together have a length 170L of about 5 mm to about 18 mm. In some examples, the length 170L can be about 8 mm to about 13 mm. In some examples, the length 170L can be about 10 mm. Accordingly, the plurality of outlets 190 can release the aqueous fluid 16 at least 10 mm from the cornea 25 of the eye 10. By releasing the aqueous fluid 16 at least 10 mm from the cornea 25, the aqueous fluid 16 can be safely absorbed by the sclera 32 and fat tissue, ultimately to be taken back by the venous system.

The length 100L of the shunt 100, from the inlet 103 to the outlets 190 can be about 10 mm to about 30 mm. In some examples, the length 100L can be about 18 mm to about 26 mm. In some example, the length 100L can be about 21 mm to about 24 mm. In some examples, the length 100L can be about 23.80 mm.

In at least one example, the surface of at least one of the vein fluidic channel 102, the body 150, and/or the plurality of outlets 190 operable to be placed, when implanted, on the eye 10 is substantially flat or substantially planar. For example, the surface of at least a portion of the shunt 100 facing the sclera 32 when implanted is substantially flat to allow the shunt 100 to lie substantially flat on the sclera 32. Accordingly, the height of the shunt 100 can be reduced and/or friction with overlying conjunctiva can be minimized.

As illustrated in FIG. 2C, the leaflets 155 are each at least partially coated with at least one drug 156 to be released into the aqueous fluid 16. In some examples, the vein fluidic channel 102, the body 150, the valve 154, and/or plurality of outlets 190 can be at least partially coated with the drug 156 to be released into the aqueous fluid 16. The vein fluidic channel 102, the body 150, the valve 154, and/or the plurality of outlets 190 can be pre-coated with the drug 156 as a therapeutic and preventative method to decrease fibrosis growth and/or reduce the risk of implant failure.

In at least one example, the drug 156 can include an anti-fibrotic agent such as mitomycin-C. Mitomycin-C is a chemotherapeutic drug which can inhibit DNA synthesis. Mitomycin-C is an anti-metabolite with anti-proliferative effect on cells showing the highest rate of mitosis by inhibiting DNA synthesis and interferes with RNA transcription and protein synthesis. Mitomycin-C functions by interfering with the formation and growth of cells. The application of mitomycin-C in surgery reduces risk of failure of the implanted shunt 100. For example, an issue for an elevated IOP postoperatively can be the formation of the encapsulation fibrosis around the valve 154. Mitomycin-C can inhibit fibroblast proliferation, inhibit scarring of filtration bleb, prolong life of bleb, and/or reduce aqueous production. However, mitomycin-C also can have complications, such as toxicity, corneal endothelial cells, changes in the ciliary body, limbal cell deficiency, and/or development of thin walled cystic blebs.

By applying the drug 156 including mitomycin-C over a large surface area along with the plurality of outlets 190, a greater short-term decrease in IOP and a significantly lower incidence of bleb scarring can be achieved in comparison with application of the drug 156 over a smaller surface area.

Figure 3:
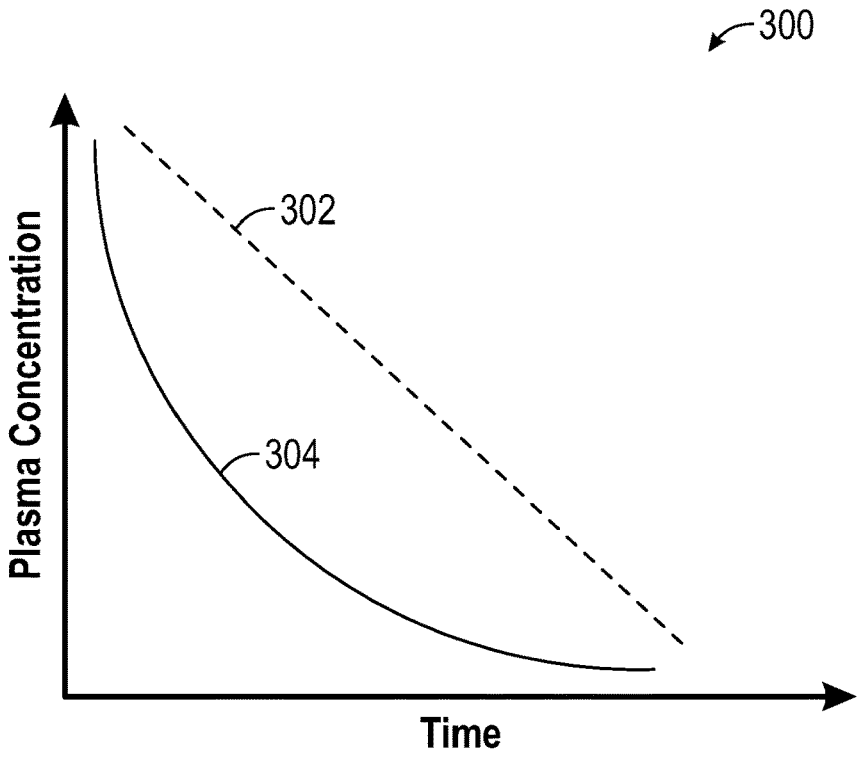
FIG. 3 is a diagram showing zero and first order drug release over time.

The drug 156 can be configured to be released over a predetermined period of time to reduce fibroblast growth, for example up to four weeks. In at least one example, the shunt 100 can be precoated with the drug 156 to release the drug 156 over a period of about 3 to 4 weeks. The drug 156 can be released by a first-order release or a zero-order release. FIG. 3 is a diagram 300 which shows the plasma concentration over time of a zero-order release 302 and a first-order release 304. With a zero-order release, the same amount of drug 156 is released per unit of time, regardless of the plasma concentration of the drug 156. With a first-order release, the same proportion of the drug 156 is released per unit of time. Accordingly, as the plasma concentration drops, the rate of release of the drug 156 also drops. By providing a lower concentration of the drug 156 over a longer exposure of time, a lower IOP and decreased fibroblast formation can be achieved. Accordingly, potential side effects and complications can be minimized.

At least one of the vein fluidic channel 102, the body 150, the valve 154, and/or the plurality of outlets 190 can be made of a bio-compatible material. In at least one example, the material can include a hydrogel. For example, the material can include an acrylic hydrogel and/or a silicone hydrogel. Hydrogels are materials composed of a network of hydrophilic polymers that can absorb water. The absorption of water renders the hydrogels more flexible and can be considered as an alternative to PMMA. The hydrogels can also swell when they absorb water. The implant procedure may be performed with a partially hydrated, flexible device, which can then swell further in the eye 10. Accordingly, the incision size can be smaller than the final size of the shunt 100.

In some examples, the materials can include poly-methyl methacrylate (PMMA), poly-hydroxyethyl) methacrylate (poly-HEMA), polyurethanes, polytetrafluoroethylene (PTFE), polyvinylidene fluoride (PVDF), liquid silicone rubber, polyethylene vinyl acetate (poly-EVA or PEVA), and/or nitinol.

In at least one example, the shunt 100 can be manufactured using any suitable method to achieve the desired drug coating and provide great support for the shunt 100 to function in the eye 10. For example, the shunt 100 can be manufactured using nanotechnology, 3D printing, and/or injection molding. In some examples, a personalized medicine approach can be utilized to improve the drug coating and overall functionality with the drug such as mitomycin-C by manufacturing the shunt 100 using a patient's stem cells and/or collagen fibers.

The design of the shunt 100 provides optimized pressure, stress, and fluid dynamics to have better longevity and regulation of IOP in the eye 10 by controlling the release of the aqueous fluid 16.

Figure 4:
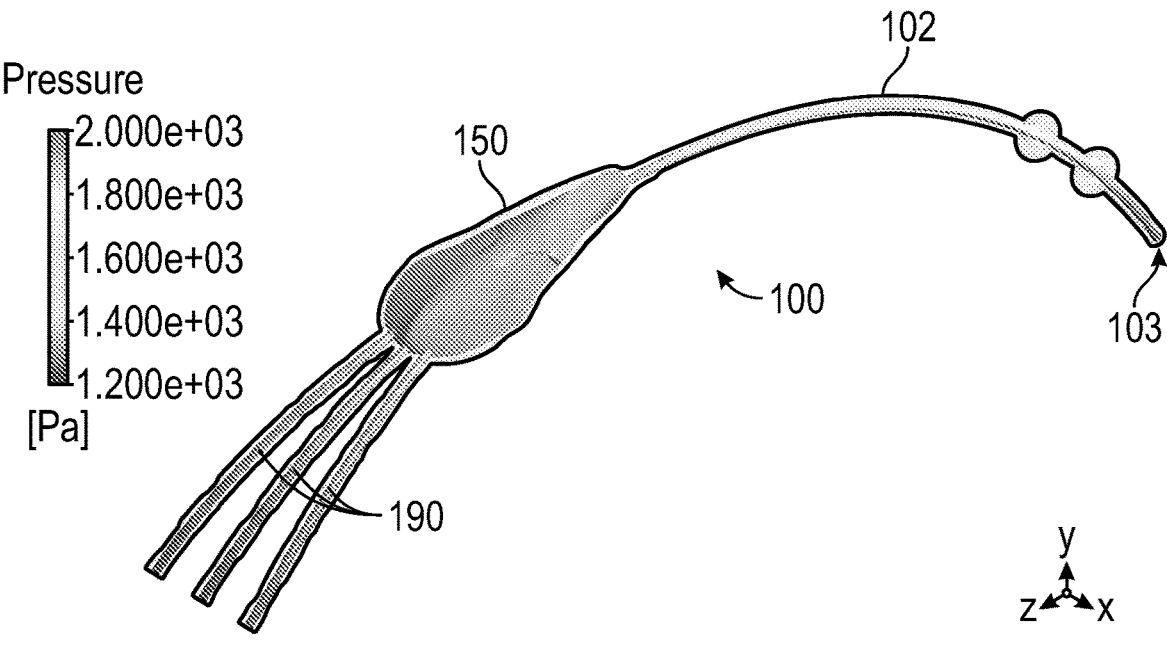
FIG. 4 illustrates pressure from fluid flowing through the shunt.

FIG. 4 illustrates the pressure distribution on the surface walls of the shunt 100. The pressure drops from 15 mmHg to 9 mmHg. The pressure drop mainly decreases within the vein fluidic channel 102 before the aqueous fluid 16 enters the entry chamber 152 of the body 150.

Figure 5:
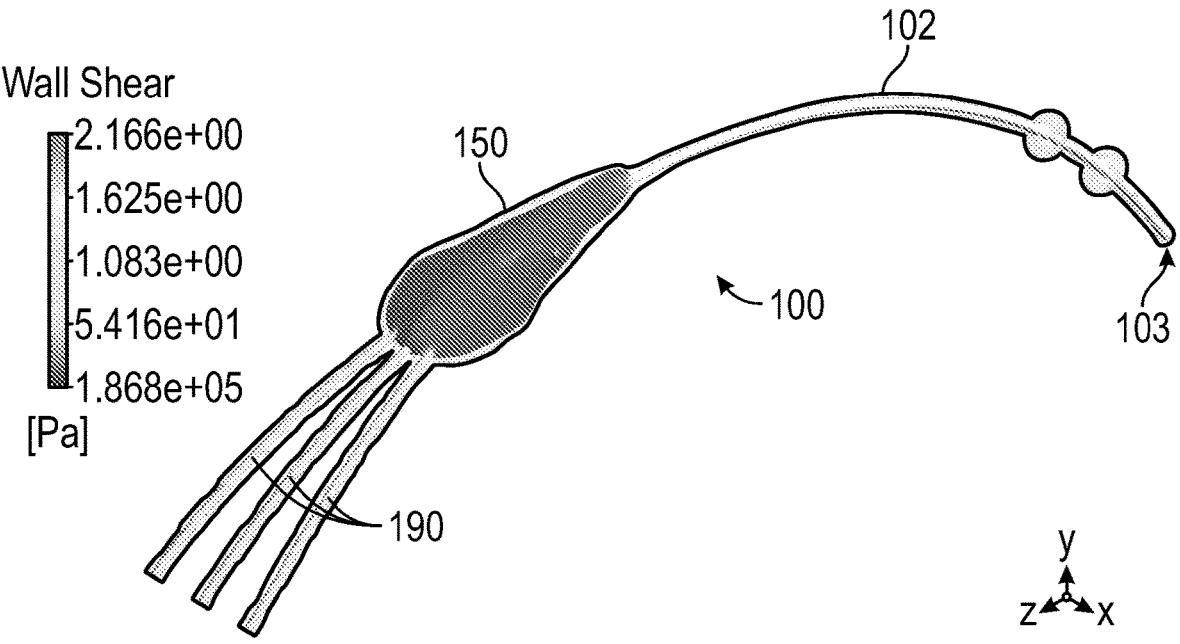
FIG. 5 illustrates shear stress on walls of the shunt from fluid flowing through the shunt.

FIG. 5 illustrates the shear stress imparted upon the shunt 100 as the aqueous fluid 16 flows through. The shear stress within the vein fluidic channel 102 is higher compared with the body 150 and the outlets 190. This can indicate that the aqueous fluid 16 has more impact on the surface wall of the vein fluidic channel 102 rather than other locations in the shunt 100.

FIGS. 6A-6C illustrate streamlines 600 of velocity magnitude of the aqueous fluid 16 at an instantaneous time when the valve 154 is open and the aqueous fluid 16 is permitted to flow through. FIG. 6A illustrates a perspective view, FIG. 6B illustrates a side view, and FIG. 6C illustrates a top view. The velocity magnitude of the aqueous fluid 16 drops after the aqueous fluid 16 enters the body 150. The lowest velocity of the aqueous fluid 16 is within the outlets 190. Accordingly, the outlets 190 can distribute the aqueous fluid 16 to the eye 10 in a slower, more controlled manner to prevent inflammation.

Figures 7A, 7B, 7C, 7D, 7E:
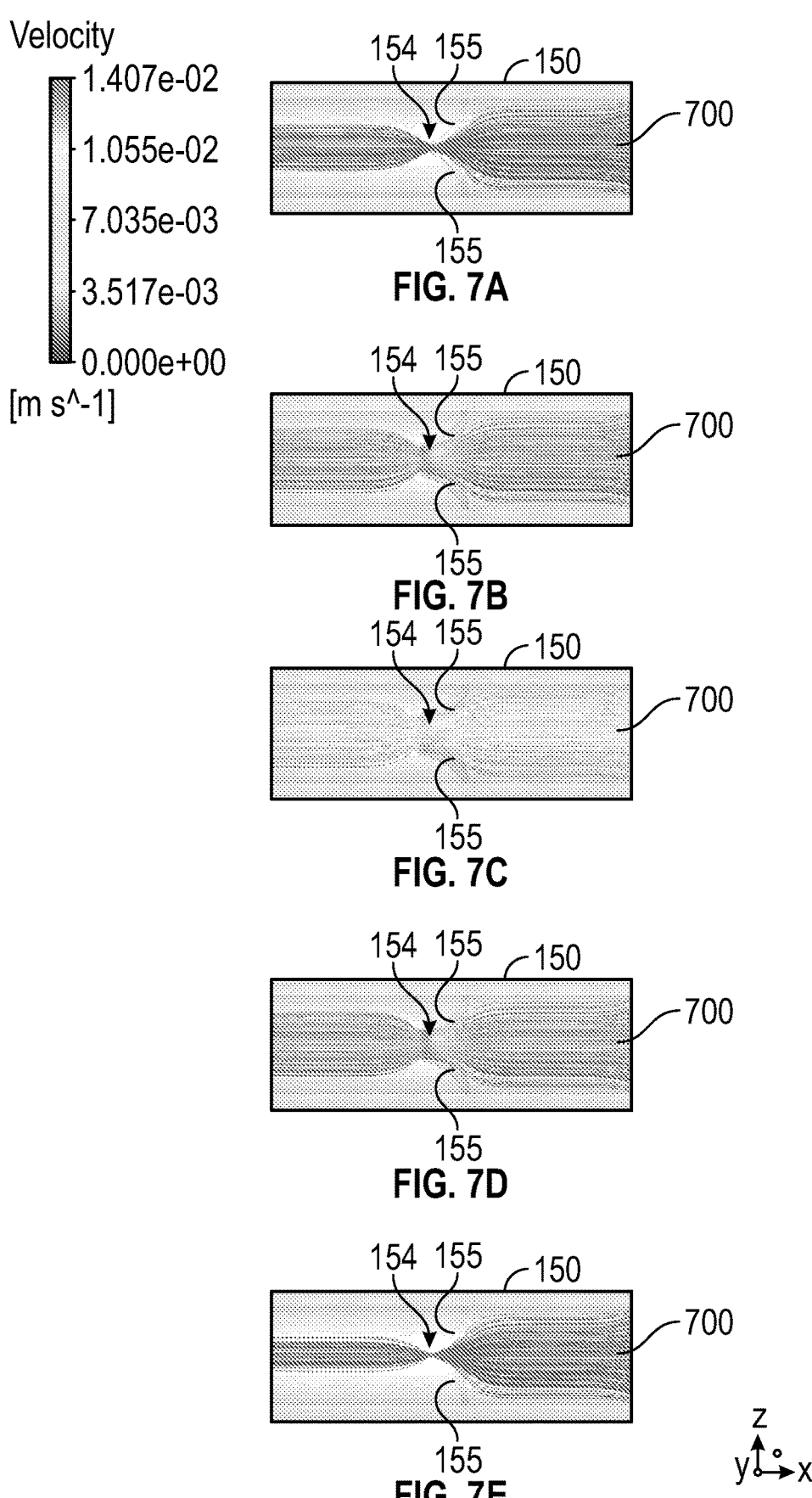
FIGS. 7A-7E illustrate velocity of fluid flowing through different configurations of the valve as the valve opens and closes.

FIGS. 7A-7E illustrate velocity streamlines 700 of the aqueous fluid 16 as the valve 154 transitions from a substantially closed configuration in FIG. 7A to an open configuration in FIG. 7C and back to a substantially closed configuration in FIG. 7E. As the flow of the aqueous fluid 16 accelerates, the valve 154 deforms and opens. At the high flow rate, the valve 154 tends to be wide open and the flow of the aqueous fluid 16 passes through the valve 154. As the flow of the aqueous fluid 16 decelerates, the valve 154 starts to close due to the decrease of the forces on the surface of the leaflets 155. The deformation of the leaflets 155 can be dependent on the thickness 155T of the leaflets 155 and/or material properties.

Figures 8A, 8B, 8C, 8D, 8E:
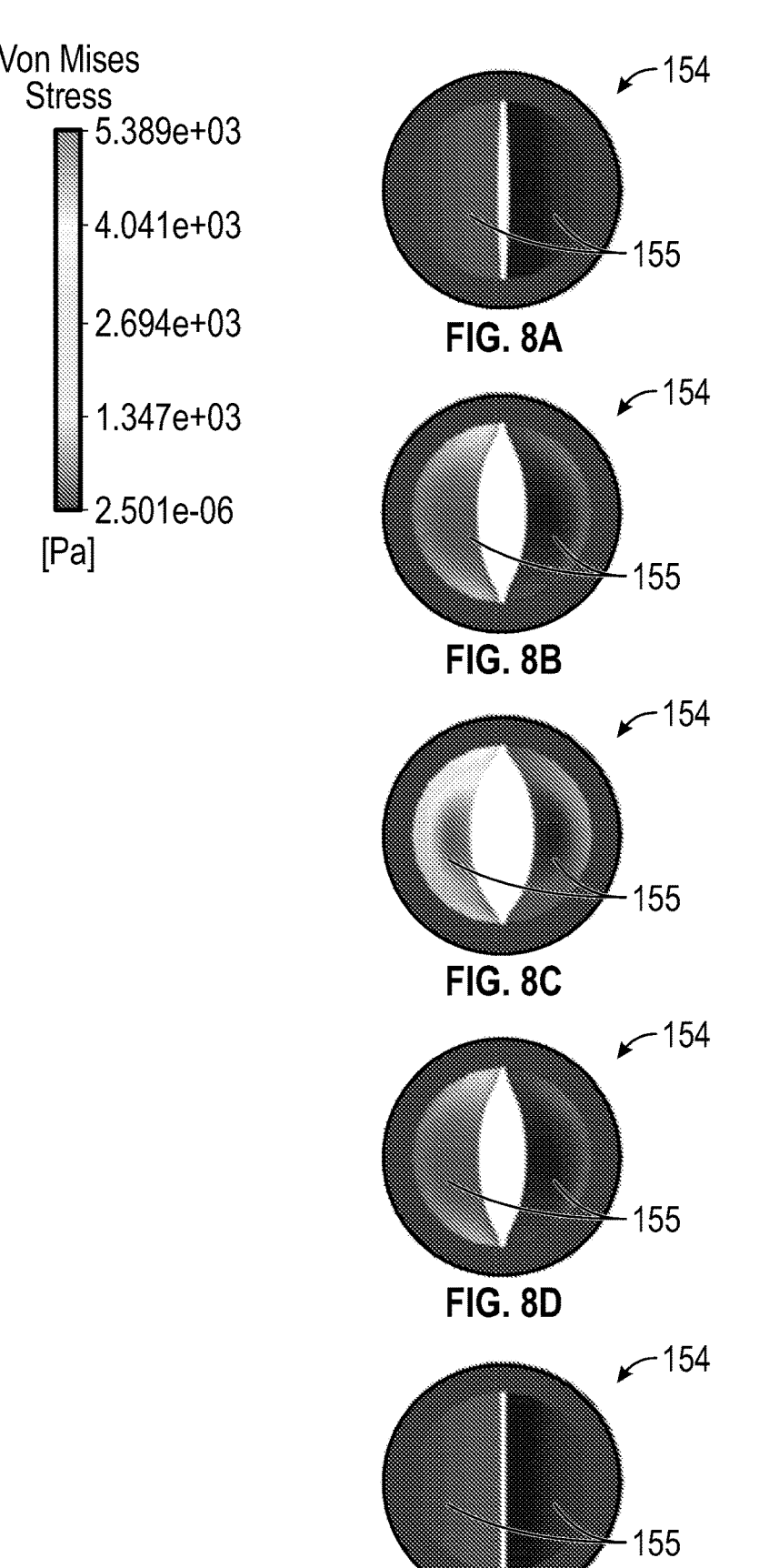
FIGS. 8A-8E illustrate stresses on the valve from the fluid as the valve opens and closes.

FIGS. 8A-8E illustrate the equivalent stresses of the valve 154 during opening and closing within one cycle, substantially closed in FIG. 8A to open in FIG. 8C to substantially closed in FIG. 8E. As illustrated in FIGS. 8A-8E, the stresses are mainly located in the base of the leaflets 155 where the leaflets 155 are connected to the inner surface wall of the body 150. Higher stress can appear in the top and bottom areas of the leaflets 155.

Figures 9A, 9B:
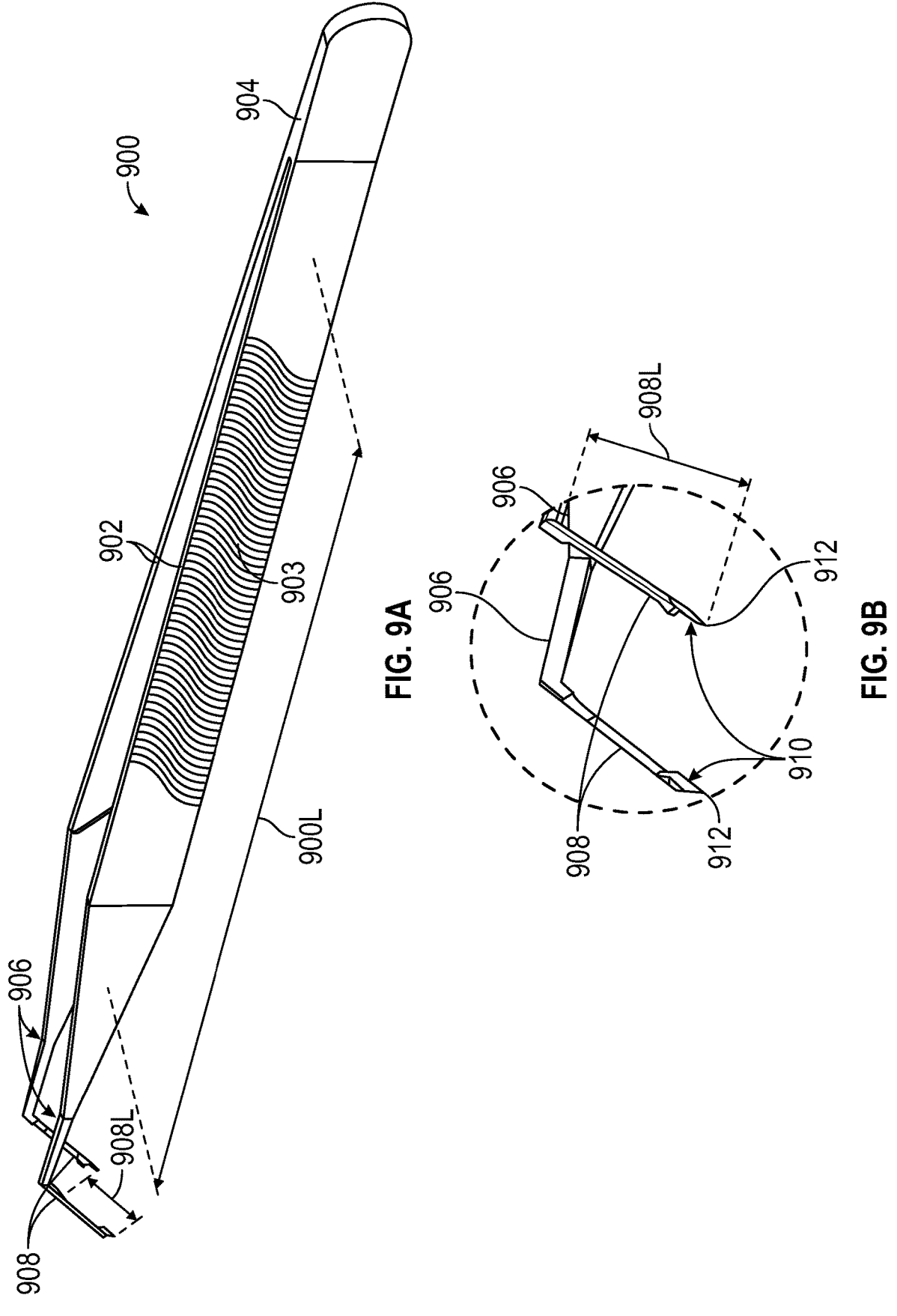
FIG. 9A illustrates implant forceps operable to implant the shunt in the eye.
FIG. 9B illustrates an enlarged view of the tips of the implant forceps of FIG. 9A.

FIGS. 9A and 9B illustrate an exemplary implant forceps 900 operable to implant the shunt 100 in the eye 10. The surgical insertion and delivery implant forceps 900 can be utilized to create a tunnel in the eye 10 such as in the sclera 32 and implant the vein fluidic channel 102 within the eye 10 with a singular action. The implant forceps 900 include a body 904, handles 902, and/or arms 906. The handles 902 can include two portions which are coupled together at the body 904. The implant forceps 900 as illustrated in FIGS.

9A and 9B is hinged at the body 904, which is disposed at the end of the implant forceps 900. In other examples, the implant forceps 900 can be hinged in the middle of the implant forceps 900 similar to scissors.

The implant forceps 900 can be formed of a biocompatible and sterile material. For example, the implant forceps 900 can be formed of stainless steel such as medical-grade stainless steel 316 and/or titanium such as titanium 64L4V. Stainless steel offers great performance, and durability in comparison to its price and availability. Titanium is a strong material and lightweight for surgeons and is also cost efficient like stainless steel. In some examples, the material of the implant forceps 900 can include one or more dopants to obtain desired properties. For example, molybdenum can be added as a dopant to stainless steel to make the material more resistant to pitting corrosion. Vanadium can be added to improve toughness and resistance to wear to refine the grain of the material. Nickel can be added to improve toughness, withstand high temperatures, and/or provide non-magnetic properties. In some examples, the implant forceps 900 can also include polymeric plastic. For example, polyether ether ketone (PEEK), polymethyl pentene (PMP), polyoxymethylene (POM), polypropylene (PP), polystyrene (PS), and/or acrylonitrile-butadiene-styrene (ABS) can be included in the material. However, if the implant forceps 900 are plastic, it is foreseen that such may be non-reusable.

The handles 902 can be arranged longitudinally in respect to one another to allow movement toward and away from one another. The handles 902 can be substantially flat on one side. In some examples, the handles 902 can be curved, rounded, and/or indented to provide a comfortable gripping surface. In at least one example, as illustrated in FIG. 9A, the handles 902 can include holding portions 903 such as grooves to assist in gripping the implant forceps 900. In some examples, the holding portions 903 can include bumps or any other suitable design to assist in gripping to implant forceps 900 and prevent slipping of the fingers. In some examples, the handles 902 can have a length of about 60 mm to about 100 mm. In some examples, the handles 902 can have a length of about 70 mm to about 90 mm. In some examples, the handles 902 can have a length of about 85 mm.

The handles 902 can taper to arms 906 which can be substantially the thickness of the tips 908. The handles 902 and the arms 906 can extend along a longitudinal axis 900L. The tips 908 extend from the arms 906 at an angle in relation to the longitudinal axis 900L to make a tunnel in the sclera 32 and enter the anterior chamber 24 of the eye 10 during implantation of the shunt 100. The tips 908, as illustrated in FIG. 9B, include blades 912 which can cut through the eye 10 to form the scleral tunnel to enter the anterior chamber 24. When closed, the tips 908 can have dimensions similar to a 23 gauge needle to decrease dissection of the eye 10, increase efficiency, and ease the procedure for physicians and patients.

In at least one example, the tips 908 can extend from the arms 906 at an angle between about 25 degrees to about 90 degrees. In some examples, the tips 908 can extend from the arms 906 at an angle between about 30 degrees to about 50 degrees. In some examples, the tips 908 can extend from the arms 906 at an angle of about 45 degrees. The angle that the tips 908 extend from the arms 906 can be provided so that the tips 908 can form the scleral tunnel comfortably for the surgeon.

In at least one example, the tips 908 can have a length 908L from about 3 mm to about 8 mm. In some examples, the tips 908 can have a length 908L from about 4 mm to about 6 mm. In some examples, the tips 908 can have a length 908L of about 5 mm to assist in controlling the depth of the scleral tunnel created in the eye 10 during implantation of the shunt 100. In some examples, the tips 908 can have a length 908L of about 6.5 mm.

The length 908L of the tips 908 designed to be the desired length of the scleral tunnel along with the hollow body 910 and the blades 912 create a simple and accurate implantation of the shunt 100.

Each of the tips 908 define one of two portions, e.g., one or two halves, of a hollow body 910, which is sized and shaped to form an elongated cylindrical enclosure. When the tips 908 are spaced from each other in an open configuration, the hollow body 910 is operable to securely receive a portion of the vein fluidic channel 102 within one of the two portions of the hollow body 910. When the tips 908 are abutted together in a closed configuration, the hollow body 910 forms the cylindrical enclosure with a top opening at a top of the cylindrical enclosure, and a bottom opening at a bottom of the cylindrical enclosure. In this manner, the hollow body 910 is operable to securely hold the vein fluidic channel 102 within the cylindrical enclosure. For example, the surgeon can grasp the vein fluidic channel 102 with the implant forceps 900 and close the handles 902. As the handles 902 and subsequently the tips 908 of the implant forceps 900 are brought closer together, the tips 908 can abut one another with portions substantially flush on each other to house the vein fluidic channel 102 inside the hollow body 910. The blades 912 of each of the tips 908 can be brought together to form a sharp blade to make an incision in the eye 10, thereby forming the tunnel in the sclera 32. For example, with the tips 908 having a length 908L of about 5 mm, the tips 908 can make a small dissection about 5 mm away from the anterior chamber 24. The implant forceps 900 can simultaneously make the incision and tunnel into the sclera 32 as well as guide the vein fluidic channel 102 inside the eye 10.

In at least one example, the hollow body 910 formed by the tips 908 can have a diameter of about 0.1 mm to about 1 mm. In some examples, the diameter of the hollow body 910 can be about 0.2 mm to about 0.4 mm. In some examples, the diameter of the hollow body 910 can be about 0.26 mm. The diameter of the hollow body 910 can correspond to the diameter of the vein fluidic channel 102 so that the vein fluidic channel 102 is securely received in the hollow body 910.

Figure 10A:
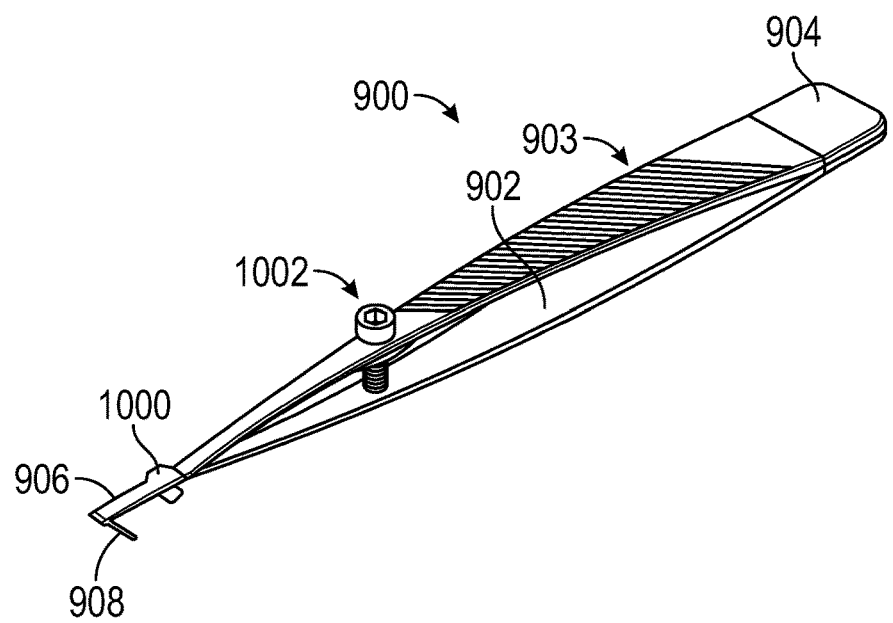
FIG. 10A illustrates another example of the implant forceps.
Figure 10B:
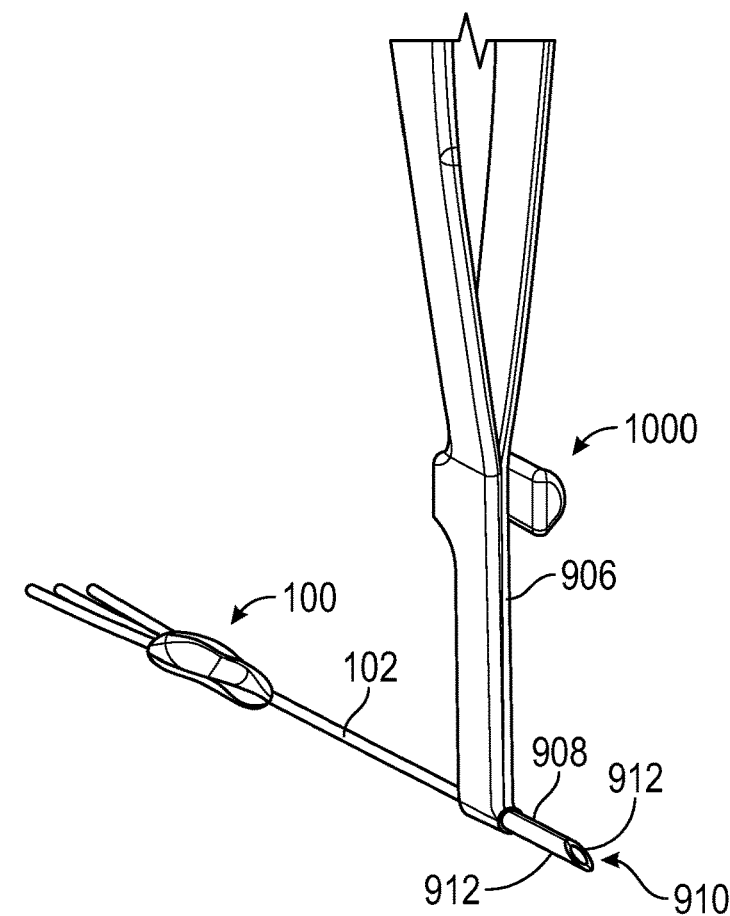
FIG. 10B illustrates an enlarged view of the tips of the implant forceps of FIG. 10A holding the shunt.

FIGS. 10A and 10B illustrate another example of implant forceps 900. In at least one example, as illustrated in FIG. 10A, an adjustable component 1002 can be included to control movement of the handles 902 towards and away from one another, and subsequently the opening and closing of the tips 908. For example, the adjustable component 1002 can include a threaded portion similar to a screw. As the adjustable component 1002 is rotated in one direction, one of the arms 902 moves up the threaded portion of the adjustable component 1002, and when the adjustable component 1002 is rotated in the opposing direction, the one of the arms 902 moves down the threaded portion of the adjustable component 1002. Additionally, the threaded portion can abut the arms 902 to prevent the arms 902 from separating or coming together unless the adjustable component 1002 is manipulated. In other examples, the adjustable component 1002 can include a ratchet mechanism where the arms 902 can be moved to bring the tips 908 closer to one another but movement of the tips 908 away from one another is prevented unless the ratchet mechanism is released. Accordingly, the adjustable component 1002 maintains a desired distance between the arms 902 to prevent inadvertent and/or undesired opening or closing of the tips 908.

As illustrated in FIGS. 10A and 10B, the tips 908 extend from the arms 906 at substantially a 90 degree angle. The angle as shown in FIGS. 10A and 10B can assist in a more comfortable implant process of the shunt 100 for the user.

A width barrier 1000 can control the maximum separation of the tips 908. In at least one example, the width barrier 1000 can be disposed proximate the arms 906. In some examples, the width barrier 1000 can be disposed between the arms 906 and the handles 902. For example, the width barrier 1000 may include an abutment portion which can abut the arms 906 and/or the handles 902 to prevent further separation or movement of the arms 906 and/or handles 902. By restricting the movement of the arms 906 and/or the handles 902, the separation of the tips 908 is restricted and controlled. In at least one example, one end of the width barrier 1000 may be coupled with one of the arms 906 and/or handles 902. The other end of the width barrier 1000 may include the abutment portion which extends out to abut the other of the arms 906 and/or handles 902 when the arms 906 and/or handles 902 are separated the desired maximum distance from one another. In some examples, a guide portion may be included which assists in maintaining alignment between the arms 906, handles 902, and/or tips 908. The guide portion may abut against a side of the two arms 906 and/or handles 902 to guide the separation and/or closure of the arms 906 and/or handles 902 and ensure the alignment of the tips 908.

FIG. 10B illustrates the tips 908 of the implant forceps 900 receiving and holding at least a portion of the vein fluidic channel 102 for implantation of the shunt 100. As shown in FIG. 10B, the vein fluidic channel 102 is received in the hollow body 910 formed by the two portions of the tips 908. Simultaneously, the tips 908 are beveled to form a sharp end to make an incision in the eye 10, thereby forming a tunnel in the sclera 32 while simultaneously inserting the shunt 100 into the eye 10. When the vein fluidic channel 102 is disposed in the desired location in the eye 10, the tips 908 of the implant forceps 900 can be separated to release the vein fluidic channel 102 and be removed from the eye 10. Accordingly, the vein fluidic channel 102 and the shunt 100 is implanted in one simple motion, minimizing the damage and trauma to the eye 10 during the procedure.

Figure 11A:
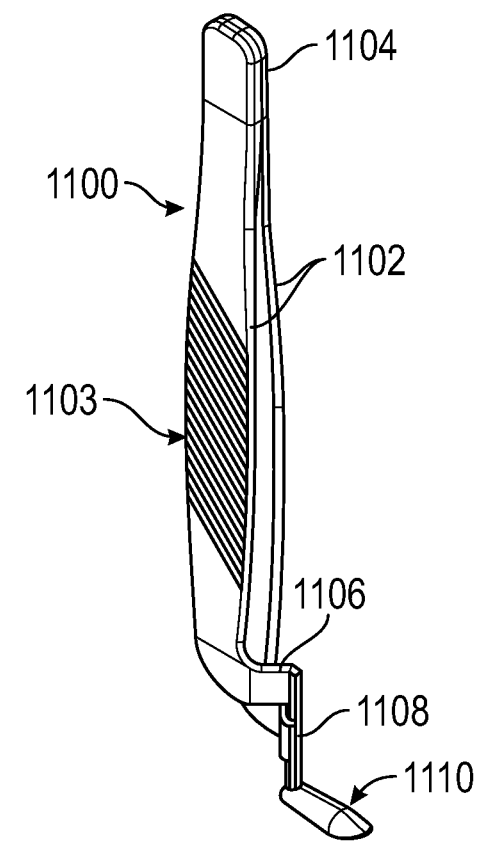
FIG. 11A illustrates placement forceps operable to position the shunt on the eye.
Figure 11B:
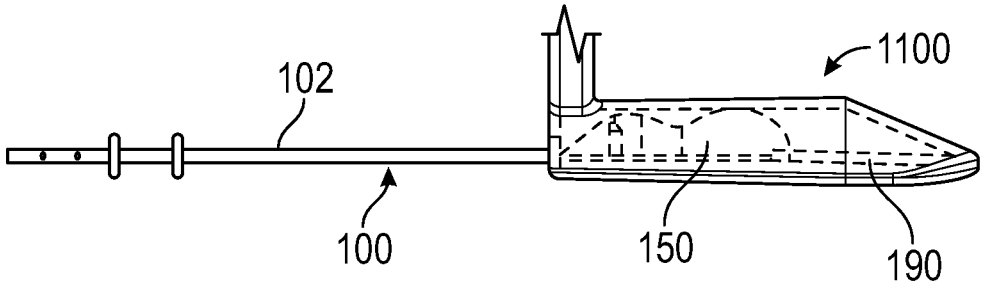
FIG. 11B illustrates an enlarged view of the tips of the placement forceps holding the shunt.

Once the vein fluidic channel 102 is inserted, placement forceps 1100, for example as illustrated in FIGS. 11A and 11B, can be utilized to hold the body 150, the outlets 190 and/or a portion of the vein fluidic channel 102 outside of the eye 10 to deliver the shunt 100 to the desired portion of the eye 10. Similar to the implant forceps 900, the placement forceps 1100 can include arms 1102 arranged longitudinally in respect to one another to allow movement toward and away from one another. The handles 1100 can include two portions which are coupled together at the body 1104. The placement forceps 1100 as illustrated in FIGS. 11A and 11B is hinged at the body 1104, which is disposed at the end of the placement forceps 1100. In other examples, the placement forceps 1100 can be hinged in the middle of the placement forceps 1100 similar to scissors.

The placement forceps 1100 can be formed of a biocompatible and sterile material. For example, the placement forceps 1100 can be formed of stainless steel such as medical-grade stainless steel 316 and/or titanium such as titanium 64L4V. Stainless steel offers great performance, and durability in comparison to its price and availability. Titanium is a strong material and lightweight for surgeons and is also cost efficient like stainless steel. In some examples, the material of the placement forceps 1100 can include one or more dopants to obtain desired properties. For example, molybdenum can be added as a dopant to stainless steel to make the material more resistant to pitting corrosion. Vanadium can be added to improve toughness and resistance to wear to refine the grain of the material. Nickel can be added to improve toughness, withstand high temperatures, and/or provide nonmagnetic properties. In some examples, the implant forceps 900 can also include polymeric plastic. For example, polyether ether ketone (PEEK), polymethyl pentene (PMP), polyoxymethylene (POM), polypropylene (PP), polystyrene (PS), and/or acrylonitrile-butadiene-styrene (ABS) can be included in the material. However, if the placement forceps 1100 are plastic, it is foreseen that such may be non-reusable.

In at least one example, as illustrated in FIGS. 11A and 11B, the placement forceps 1100 can include a bend portion 1106 which connects the handles 1102 with arms 1108. In at least one example, the arms 1108 may extend substantially parallel to the longitudinal axis of the handles 1102. In some examples, the arms 1108 may extend at an angle in relation to the longitudinal axis of the handles 1002. As illustrated in FIGS. 11A and 11B, the bend portion 1106 forms substantially a 90 degree angle from the longitudinal axis of the handles 1102 such that the arms 1108 are positioned on a different plane than the handles 1102. The arms 1108 being on a different plane than the handles 1102 can provide a more comfortable configuration for the user to position the shunt 100 on the eye 10.

The tips 1110 of the placement forceps 1100 can each form a hollow portion where together, the two tips 1100 form a delivery case operable to receive and release at least a portion of the shunt 100 to place the shunt 100 at the desired location on the eye 10. For example, as illustrated in FIGS. 11A and 11B, the tips 1100 can be formed in the delivery case corresponding to the shape of the shunt 100. For example, the delivery case of the tips 1100 can have a shape to receive and hold within the delivery case the body 150 of the shunt 100 as shown in FIG. 11B. In some examples, the delivery case can also receive and hold the outlets 190. In some examples, the delivery case can also receive and hold a portion of the vein fluidic channel 102. The delivery case of the tips 1100 can have a smooth, rounded tip to reduce friction and allow for minimal tissue injury. Also, the tips 1100 can protect the shunt 100, for example the body 150 and/or the outlets 190, from any external mechanism stresses.

In at least one example, the tips 1100 when closed together can have a width of about 2 mm to about 8 mm. In some examples, the tips 1100 closed together can have a width of about 3 mm to about 5 mm. In some examples, the tips 1100 closed together can have a width of about 4.07 mm. The width of the tips 1100 when closed together can be adjusted to accommodate the width of the portion of the shunt 100 to be received in the tips 1100, for example the width of the body 150 and the outlets 190. In at least one example, the tips 1100 can have a length of about 4 mm to about 16 mm. In some examples, the length of the tips 1100 can be about 7 mm to about 12 mm. In some examples, the length of the tips 1100 can be about 10.20 mm. The length of the tips 1100 can be adjusted to accommodate the length of the shunt 100 to be received in the tips 1100, for example the length of the body 150 and the outlets 190.

The bottom portion of the tips 1100 may have a curvature to substantially correspond to the curvature of the eye 10. Accordingly, the curvature allows for minimal dissection of the conjunctiva and/or Tenon's capsule, thereby making the process of creating a pocket to receive the shunt 100 more intuitive and natural for the user. Instead of requiring another pair of forceps or surgical scissors to create a pocket in the eye 10 to receive the shunt 100, the user can wiggle the rounded smooth end of the tips 1100 when closed together back and forth to create the pocket in the eye 10 to receive the shunt 100.

In at least one example, the implant forceps 900 and the placement forceps 1100 can be included in one device. In some examples, only some components of the implant forceps 900 such as the tips 908 and/or the placement forceps 1100 such as the tips 1100 are included in a single device to minimize the amount of coordination required between implanting the vein fluidic channel 102 and placing the body 150 and outlets 190 of the shunt 100.

With the designs of the implant forceps 900 and/or the placement forceps 1100, damage to vessels, tissues, and/or the shunt 100 can be reduced and minimized. The safety profile can be increased while the surgical time, intraoperative tissue damage, and/or postoperative tissue scarring can be decreased.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. A shunt operable to be implanted on an eye, the shunt comprising:

a vein fluidic channel operable to be in fluid communication with an interior of the eye and operable to receive aqueous fluid from the interior of the eye;

a body fluidly coupled with the vein fluidic channel;

a valve disposed within the body, the valve operable to regulate intraocular pressure (IOP) in the eye by opening and closing based on pressure from the aqueous fluid, wherein the valve includes two leaflets, wherein a base of each of the leaflets has a base thickness, and wherein a thickness of the two leaflets tapers towards an end opposite the base, and wherein the valve further comprises a commissure where the respective ends of the two leaflets opposite the bases of the two leaflets are configured to meet when the valve is closed;

an exit chamber configured to receive aqueous fluid exiting the valve when the valve is open; and a plurality of outlets in fluid communication with the exit chamber, the plurality of outlets operable to release aqueous fluid from the exit chamber to a sclera of the eye.

2. The shunt of claim 1, wherein each of the two leaflets have a length that is two times a width of an inner lumen of the body.

3. The shunt of claim 1, wherein the end opposite the base of each of the leaflets has an end thickness that is ⅓ the base thickness.

4. The shunt of claim 1, wherein the two leaflets are operable to deform and separate from one another upon exposure to a predetermined amount of pressure from the aqueous fluid.

5. The shunt of claim 1, wherein at least one of the vein fluidic channel, the body, the valve, and/or the plurality of outlets is at least partially coated with at least one drug to be released into the aqueous fluid.

6. The shunt of claim 5, wherein the drug includes mitomycin-C.

7. The shunt of claim 5, wherein the drug is configured to be released over a predetermined period of time.

8. The shunt of claim 7, wherein the predetermined period of time is up to four weeks.

9. The shunt of claim 1, further comprising:

at least two retainers extending from the vein fluidic channel, the at least two retainers operable to maintain positioning of the vein fluidic channel.

10. The shunt of claim 9, wherein the at least two retainers are substantially circular and extend radially from the vein fluidic channel.

11. The shunt of claim 9, wherein the at least two retainers are positioned such that, when implanted, a first one of the at least two retainers is operable to be positioned on a trabecular meshwork surface of the eye and a second one of the at least two retainers is operable to be positioned on a scleral surface of the eye.

12. The shunt of claim 1, wherein a surface of at least one of the vein fluidic channel, the body, and/or the plurality of outlets operable to be placed, when implanted, on the eye is flat.

13. The shunt of claim 1, wherein at least one of the vein fluidic channel, the body, the valve, and/or the plurality of outlets is made of a bio-compatible material.

14. The shunt of claim 13, wherein the bio-compatible material includes a hydrogel.

15. The shunt of claim 13, wherein the bio-compatible material includes an acrylic hydrogel or a silicone hydrogel.

16. A system comprising:

the shunt as recited in claim 1; and a forceps operable to implant the shunt in the eye.

17. The system of claim 16, wherein the forceps include tips collectively forming a hollow body operable to receive, when the tips are in a closed configuration, the vein fluidic channel.

18. The shunt of claim 1, wherein the plurality of outlets comprise a plurality of pores in fluid communication with the exit chamber.

19. The shunt of claim 1, wherein the plurality of outlets comprise fluidic channels.

\* \* \* \* \*